(12) United States Patent
Weinschenk, III

(10) Patent No.: US 6,555,030 B1
(45) Date of Patent: Apr. 29, 2003

(54) METHOD FOR MAKING AN ACCOMMODATING INTRAOCULAR LENS

(75) Inventor: Joseph I. Weinschenk, III, Laguna Niguel, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/552,746

(22) Filed: Apr. 21, 2000

(51) Int. Cl.[7] ................................................ B29D 11/00
(52) U.S. Cl. .......................................... 264/1.7; 264/2.6
(58) Field of Search ........................... 264/1.1, 1.7, 2.7, 264/2.6

(56) References Cited

U.S. PATENT DOCUMENTS

| | | | |
|---|---|---|---|
| 4,781,718 A | * 11/1988 | Lindstrom | ...................... 623/6 |
| 4,834,754 A | 5/1989 | Shearing | |
| 4,921,497 A | * 5/1990 | Sulc et al. | |
| 4,961,746 A | * 10/1990 | Lim et al. | ................... 264/1.7 |
| 5,217,491 A | 6/1993 | Vanderbilt | |
| 5,326,506 A | 7/1994 | Vanderbilt | |

FOREIGN PATENT DOCUMENTS

| | | |
|---|---|---|
| EP | 0331457 | 3/1989 |
| EP | 0552528 A1 | 1/1992 |
| EP | 0920980 A2 | 9/1998 |

\* cited by examiner

*Primary Examiner*—Mathieu D. Vargot
(74) *Attorney, Agent, or Firm*—Robert J. Baran; Peter Jon Gluck

(57) ABSTRACT

A method of making an intraocular lens having an optic portion joined to a haptic portion by a flexible element which comprises the steps of:

(e) forming a core of a material suitable for use as said optic portion;

(f) reacting said core to provide a first composite of said optic portion and said flexible element bonded thereto;

(g) reacting said flexible element with a material suitable for use as said haptic portion to provide a second composite; and (h) machining said second composite to form said intraocular lens.

20 Claims, 3 Drawing Sheets

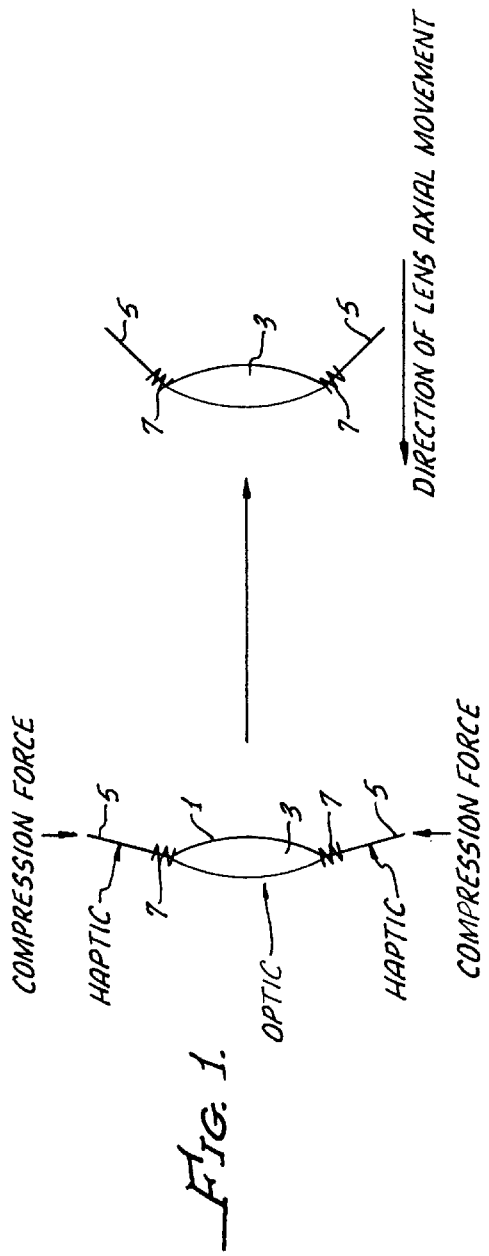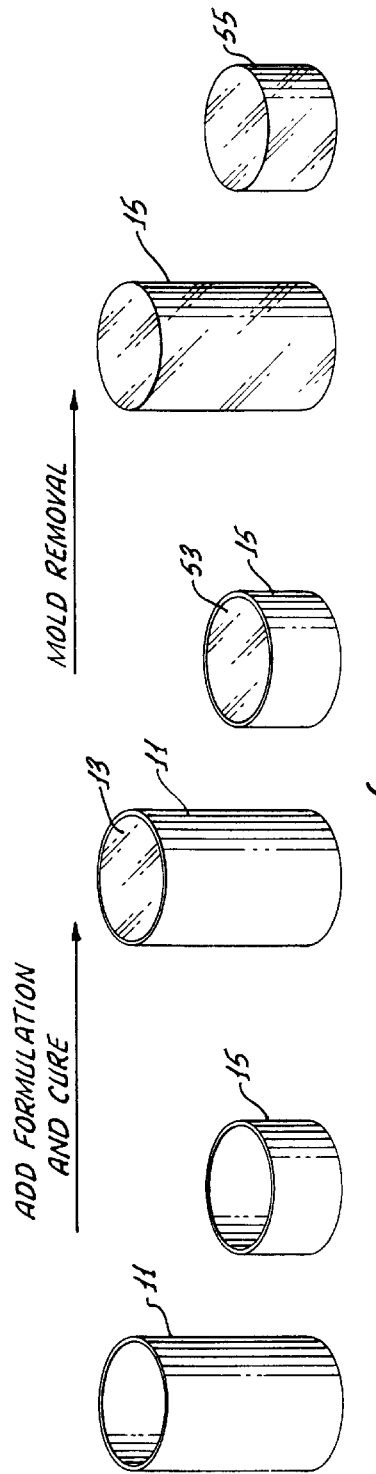

METHOD FOR MAKING AN ACCOMMODATING INTRAOCULAR LENS

BACKGROUND OF THE INVENTION

1. Field of the Invention

The present invention relates to the field of intraocular lens and, in particular, intraocular lenses that move axially to alleviate the condition of presbyopia when implanted in the eye of a patient.

2. Description of the Art

Presbyopia is the medical term for the condition in which an individual loses the ability to focus on nearby objects such as the words in a book.

Research is currently underway to address this medical condition. In particular, research is focused on the replacement of the "malfunctioning" natural lens with an artificial one that could move axially or change shape so that the patient would have restored accommodating ability.

An intraocular lens, i.e. an IOL, that moves axially when subjected to the muscular forces within the eye, will accommodate to deliver light to the proper spot on the retina. In other words, the IOL would deliver "focusable" vision by axial movement.

In such an IOL it is desirable for the lens to "bend" at the haptic-optic junction in order to achieve the axial movement required. However, since the compression force in the eye is known to be very weak, the material strength at the haptic-optic junction must be low.

Therefore, rigid IOL materials, comprising a single material for both the optic and the haptic, like polymethylmethacrylate or PMMA, would not be suitable for providing an IOL that would accommodate as described. Also, typical "soft" acrylic materials, which have a tensile strength about 840 psi, may also be too strong to provide both the optic and the haptic portions of an accommodating IOL. Conversely, known "soft" IOL materials like silicones or acrylic hydrogels are likely too soft and, therefore, a lens made with these types of materials, as the haptics, would not function as desired. Instead, the haptics of these lenses might bend anywhere from the haptic-optic junction to the lens periphery.

Thus, it is an object of the present invention to provide an accommodating IOL which will bend at the optic-haptic junction to alleviate presbyopia or other ocular conditions wherein light is not delivered to the proper spot on the retina.

BRIEF SUMMARY OF THE INVENTION

The present invention provides a method of making an intraocular lens having an optic portion joined to a haptic portion by a flexible element which comprises the steps of:

(a) forming a core of a material suitable for use as said optic portion;

(b) reacting said core to provide a first composite of said optic portion and said flexible element bonded thereto;

(c) reacting said flexible element with a material suitable for use as said haptic portion to provide a second composite; and (d) machining said second composite to form said intraocular lens.

In one embodiment of the invention the first composite is provided by polymerizing a first polymerizable material capable of forming said flexible element to form an outer layer about said core.

In a second embodiment, the first composite is provided by reacting the core, at the surface thereof, e.g. by hydrolyzing the surface core material, to form said flexible element.

In said first embodiment, the core may be placed in a mold, said first polymerizable material may be placed in said mold about said core and said first polymerizable material may be polymerized around said core.

In either embodiment, a second polymerizable material, capable of forming said haptic portion, is polymerized about said first composite to form an outer layer about said first composite.

The second composite is preferably provided by positioning said first composite in a mold, placing a second polymerizable material in said mold about said first composite and polymerizing said second polymerizable material.

BRIEF DESCRIPTION OF THE DRAWINGS

FIG. 1 shows the IOL prepared by the method of the present invention.

FIG. 2 shows the method of forming the core used in preparing the above IOL.

DETAILED DESCRIPTION OF THE INVENTION

An intraocular lens 1 as shown in FIG. 1 includes an optic 3 and one or more haptics 5 joined to said optic 3 by flexible portion 7 which is softer or more flexible than either the optic 3 or the haptics 5. As shown, when a compressive force is applied to the haptics 5, the optic 3 moves axially. Thus, when implanted in the eye of a patient, the optic may accommodate to focus light on the patient's retina.

Figure 3A:
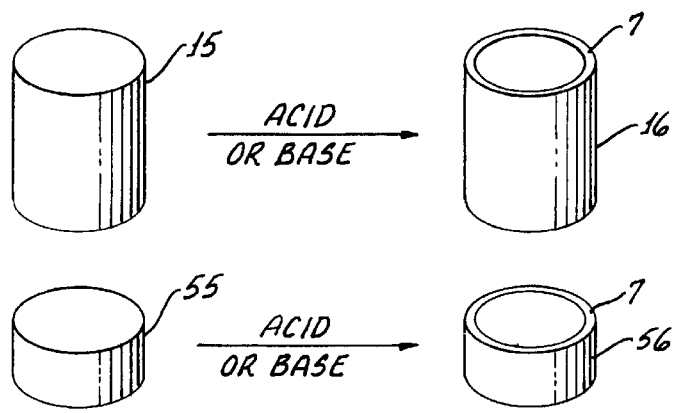
FIGS. 3a and 3b show the methods for forming the first composite used in preparing the IOL of the present invention.
Figure 3B:
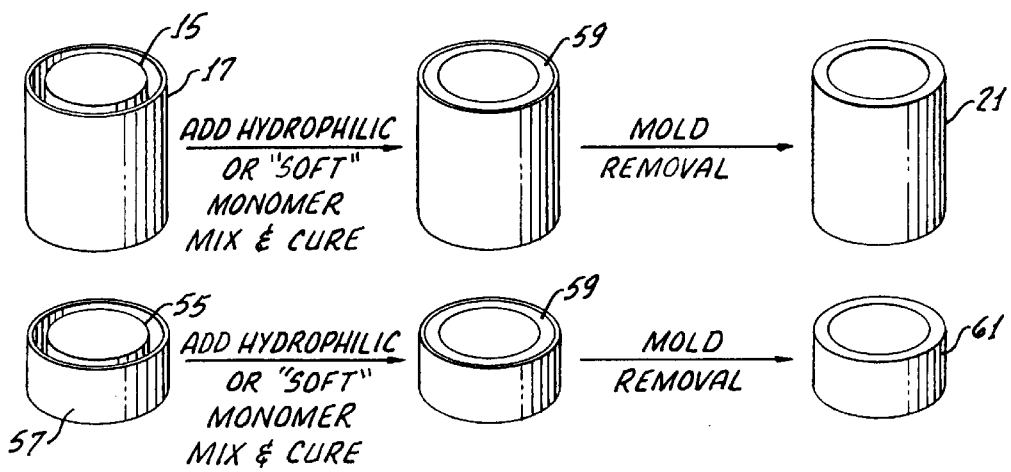
Figure 4:
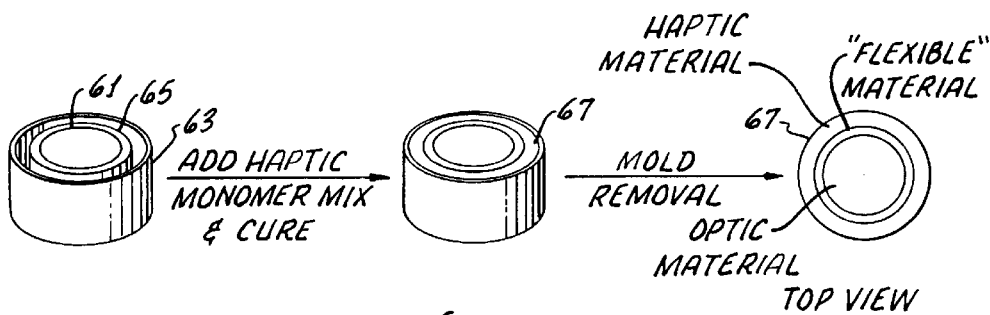
FIG. 4 shows the method for preparing the second composite used in preparing the IOL of the present invention.

Intraocular lens 1 may be prepared as shown in FIGS. 2 through 4.

As shown in FIG. 2, a tube 11 or cup 51 is utilized as a mold to prepare the core that is utilized as the center optic material in the finished IOL. An appropriate liquid monomer mixture, including monomers and an initiator, is placed in the respective tube or cup mold and cured with thermal or ultraviolet (UV) or another energy source, as known in the art, to yield a solid core as shown in 13 and 53.

A suitable monomer mixture for forming said core may include 99.5%, by weight, methylmethacrylate, and 0.5%, by weight, of a UV absorber such as benzotriazole. The molds are then removed to provide the core as a rod 15 or button 55.

As shown in FIGS. 3a and 3b, the flexible element 7 that is affixed to the optic portion in the IOL of the invention, may be provided by one of two methods.

In the first method, as shown in FIG. 3a, rod 15 or button 55 is treated with a strong acid or base to hydrolyze the surface thereof and thereby provide the first composite 16 or 56, respectively. In such hydrolysis, a portion of the surface ester groups on the methylmethacrylate homopolymer are converted to the corresponding carboxylic acid groups, as shown. The hydrolyzed surface will soften when contacted with aqueous liquids, thus, providing the flexible element in the IOL of the invention. A suitable strong base might be a 50%, by weight, aqueous NaOH solution. A suitable strong acid might be a 70%, by weight, aqueous $H_2SO_4$ solution. The hydrolysis may be continued until the surface of said rod 15 or button 55 is hydrolyzed to a depth of about 0.5 mm or more, depending on the desired thickness of the flexible element portion 7 of the first composite 16 or 56.

Alternatively, as shown in FIG. 3b, rod 15 or button 55 is placed in the center of an oversized mold 17 and 57, respectively, and a hydrophilic or soft monomer mixture 19 and 59, respectively, is poured into the space between the mold and the rod 15 or button 55. The hydrophilic or soft monomer mixture is cured with the appropriate energy source as described above to convert rod 15 or button 55 into the first composite 21 or 61, respectively.

A suitable hydrophilic monomer mixture may include 99%, by weight, hydroxyethyl methacrylate (HEMA)and 1%, by weight, of a crosslinker, such as ethyleneglycol-dimethacrylate (EGDMA) as well as a peroxide or azo compound as an initiator. A suitable soft monomer mixture may include 99%, by weight, ethylacrylate (EA) and 1%, by weight, of a crosslinker such as EGDMA.

In this embodiment of the present invention, the flexible element 7, formed from the hydrophilic monomer mixture functions as the hydrolyzed surface of the first composite 16 or 56, discussed above. That is the polymer resulting from the hydrophilic monomer mixture softens when contacted with aqueous liquids to provide the flexible element 7. In contrast, polymer resulting from a soft monomer mixture is, itself, more flexible than the rod 15 or button 55 and the later added haptics to thereby bend as required in the accommodating IOL of the invention.

In said alternative method for preparing said first composite, it is preferable to allow the added hydrophilic or soft monomer mix to diffuse into the button 55 or rod 15 for a certain amount of time before initiating the cure. This results in an interpenetrating network between the core and hydrophilic or soft outer layer which becomes the flexible element, thus increasing the strength of the "bond" between them.

Finally, as shown in FIG. 4, the first composite which is designated as 16, 56, 21 or 61 in the embodiments set forth in FIGS. 3a and 3b, is provided with an element for forming the haptic at the outer part of the first composite. In the final product, an IOL, this material has the desirable properties possessed by the haptics and/or "skirts" that surround the optic portion in one-piece IOL lens designs.

The first composite is placed in the center of an oversized mold 63 and then the liquid monomer mix 65 is added into the mold to fill the void around the first composite. The liquid monomer mix 65 is cured with the appropriate energy source, and then mold removal is effected to yield the second composite 67. This is illustrated for the first composite 61, only, in FIG. 4, but the other examples of said first composite, i.e. 16, 56 or 21, could be treated in the same manner to form a haptic material thereabout.

An example rigid composition for the haptic material would be 100% MMA

An example flexible composition for the haptic material would be

| |
|---|
| 58% ethyl acrylate (EA) |
| 29% ethyl methacrylate (EMA) |
| 9% 2,2,2-trifluoroethyl methacrylate (TFEMA) |
| 3.5% EGDMA |
| 0.5% UV Absorber (e.g., benzotriazole) |

Figure 5A:
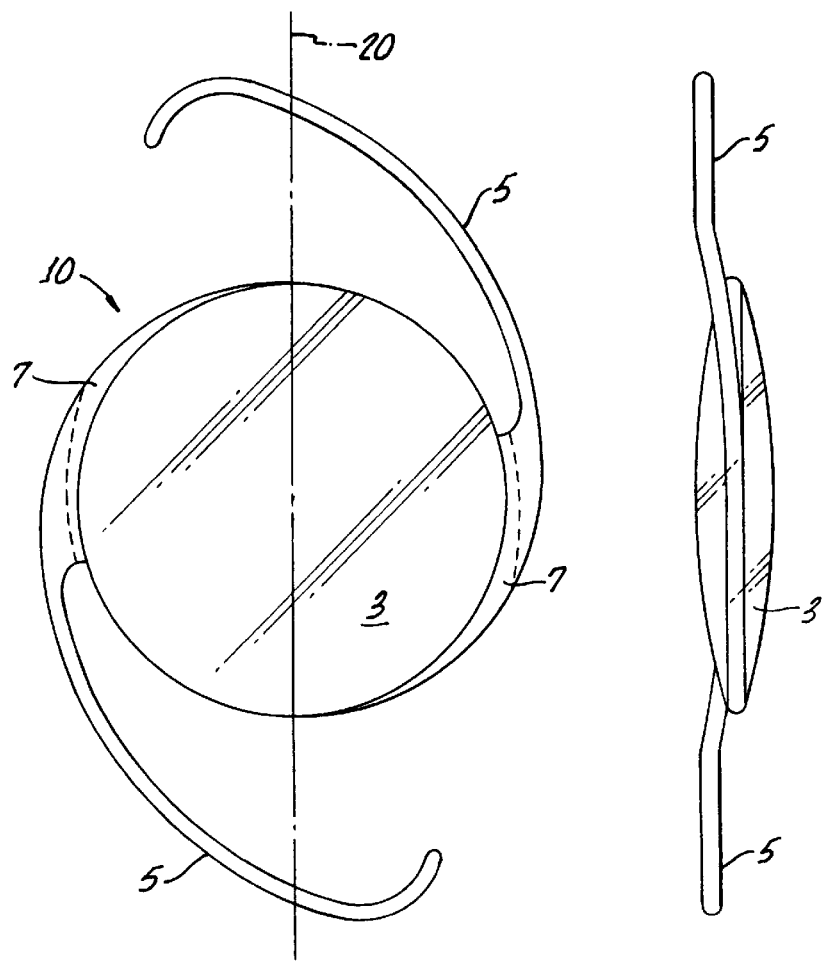
FIG. 5a shows a "three piece" IOL as may be fabricated with the method of the present invention.
Figure 5B:
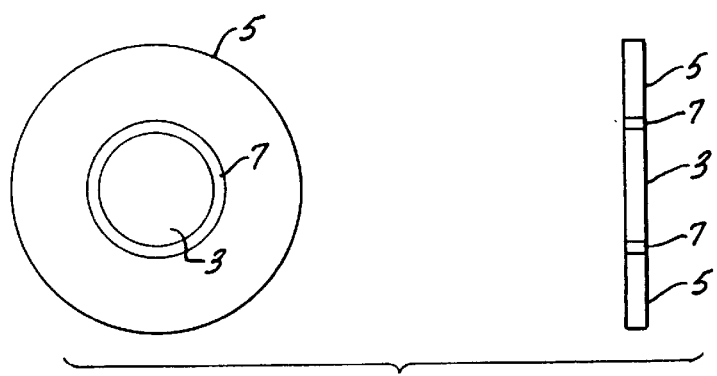
FIG. 5b shows a "one piece" IOL, having a haptic skirt, as may be fabricated with the method of the present invention.

Manufacture of an IOL from said second composite 67 is effected by lathing the button-shaped first composite 67, shown in FIG. 4, or by cutting a button from a first composite in the form of a rod, e.g. 16 or 21, first, and the resultant button being like that just noted in FIG. 4, may, be lathed/milled to resemble a 3-piece IOL as shown in FIG. 5a, or a one-piece IOL with a "skirt" as shown in FIG. 5b.

While illustrated above for specific polymers that can be used to form the optic portion, the flexible element and the haptic portion, it will be appreciated that other polymers may be used provided only that the flexible element be softer than either the optic portion or the haptic portion so that the optic portion may move axially when subject to compressive force by the muscles of the implanted eye to focus light properly on the retina.

For example the optic portion may be one of the following polymers:
-poly(methyl methacrylate)
-copolymer of

| | |
|---|---|
| 2-phenoxyethyl acrylate | 70% |
| 2-phenoxyethyl methacrylate | 28% |
| EGDMA | 2% |

-copolymer of

| | |
|---|---|
| 2-phenoxyethyl acrylate | 32.5% |
| 2-phenoxyethyl methacrylate | 48.8% |
| 3,5,5-trimethylhexyl acrylate | 14.7% |
| Ethylene glycol dimethacrylate | 2.0% |
| UV absorber | 2.0% |

-copolymer of

| | |
|---|---|
| Ethyl acrylate | 55% |
| Ethyl methacrylate | 50% |
| 2,2,2-trifluoroethyl methacrylate | 10% |
| Ethylene glycol dimethacrylate | 3.5% |
| UV absorber | 1.5% |

-copolymer of crosslinked polydimethyldiphenylsiloxane

The flexible element may comprise one of the following polymers.
-copolymers, including a lightly crosslinked copolymers, comprised of acrylate and methacrylate monomers, and whose Tg is no greater than about 13° C., for example:
-copolymers, including a lightly crosslinked copolymers, of
  Butyl acrylate or hexyl acrylate and
  Methyl methacrylate or ethyl methacrylate
-copolymer, including a lightly crosslinked copolymer, of

| | |
|---|---|
| 2-hydroxyethyl methacrylate | 71% |
| N-vinyl pyrrolidone | 29% |

-copolymer, including a lightly crosslinked copolymer, of

| | |
|---|---|
| ethyl acrylate | 17% |
| 2-hydroxyethyl methacrylate | 69% |
| N-vinyl pyrrolidone | 14% |

-copolymer, including a lightly crosslinked copolymer, of

| ethyl acrylate | 6% |
|---|---|
| 2-phenoxyethyl acrylate | 29% |
| N-vinyl pyrrolidone | 59% |
| 3,5,5,-trimethylhexylmethacrylate | 6% |

-copolymer of

| ethyl acrylate | 59.7% |
|---|---|
| N-vinyl pyrrolidone | 39.8% |
| tetraethylene glycol dimethacrylate | 0.25% |

-copolymer of

| ethyl acrylate | 28.6% |
|---|---|
| methyl methacrylate | 14.3% |
| dimethyl acrylate | 56.8% |
| tetraethylene glycol dimethacrylate | 0.4% |

-copolymer of very lightly crosslinked polydimethyldiphenylsiloxane

The haptic may comprise one of the following polymers.
-poly(methylmethacrylate)
-crosslinked copolymer comprised of acrylate/methacrylate monomers with a Tg of at least 40° C.
-copolymer of crosslinked polydimethyldiphenylsiloxane The embodiments above are intended to be illustrative of the invention, and it is expected that those of ordinary skill in the art may, in view of the teachings contained hereinabove, be able to modify the embodiments illustrated herein. It is intended to cover all such modifications which fall within the spirit and scope of the invention as defined by the claims appended hereto.

What is claimed is:

1. A method of making an accommodating intraocular lens having an optic portion joined to a haptic portion by a flexible element which allows the optic portion to move axially in the eye when subjected to compressive force which comprises the steps of:
   (a) forming a core of a material suitable for use as said optic portion;
   (b) polymerizing about said core a first polymerizable material for forming a flexible element to provide a first composite of said optic portion and said flexible element bonded thereto;
   (c) reacting said flexible element with a material suitable for use as said haptic portion to provide a second composite; and
   (d) machining said second composite to form said intraocular lens.

2. The method of claim 1 further comprising positioning said core in a mold, placing said first polymerizable material in said mold about said core, and polymerizing said first polymerizable material.

3. The method of claim 2 further comprising the step of polymerizing about said first composite a second polymerizable material, capable of forming said haptic portion, to form an outer layer about said first composite.

4. The method of claim 3 further comprising positioning said first composite in a mold, placing said second polymerizable material in said mold about said composite, and polymerizing said second polymerizable material.

5. The method of claim 1 wherein said optic portion comprises a high refractive material.

6. The method of claim 5 wherein said high refractive material is selected from the group consisting of polymethylmethacrylate, and copolymers of high refractive index monomers selected from the group consisting of 2-phenoxyethyl acrylate, 2-phenoxyethyl methacrylate, benzyl acrylate, benzyl methacrylate, 2-phenylethyl acrylate, 2-phenylethyl methacrylate, N-vinyl carbazole, 3-phenylpropyl acrylate, and 3-phenylpropyl methacrylate.

7. The method of claim 1 wherein said flexible element is selected from the group consisting of poly(ethylacrylate) homopolymer, polymers and copolymers of n-propyl acrylate, n-butyl acrylate, n-hexyl acrylate, lightly crosslinked poly(dimethyldiphenylsiloxane), and lightly crosslinked poly(dimethylsiloxane).

8. The method of claim 1 wherein said haptic portion is selected from the group consisting of poly(methylmethacrylate), crosslinked copolymers comprised of acrylate/methacrylate monomers with a Tg of at least 40° C. and copolymers of crosslinked polydimethyldiphenylsiloxane.

9. The method of claim 1 wherein said flexible element is more flexible than said optic portion and said haptic portion.

10. The method of claim 1 wherein said optic portion is polymethylmethacrylate.

11. The method of claim 1 wherein said flexible element is polyethylacrylate.

12. The method of claim 1 wherein said haptic portion is polymethylmethacrylate.

13. The method of claim 4 further comprising providing said second composite as a rod having said material suitable for use as said haptic portion as an outer layer around said first composite.

14. The method of claim 13 further comprising cutting a disc from said rod and removing a portion of said outer layer of said rod to form at least one haptic portion.

15. A method of making an accommodating intraocular lens having an optic portion joined to a haptic portion by a flexible element which allows the optic portion to move axially in the eye when subjected to compressive force which comprises the steps of:
   (a) forming a core of a material suitable for use as said optic portion;
   (b) hydrolyzing the surface of said core material to provide a first composite of said optic portion and said flexible element bonded thereto;
   (c) reacting said flexible element with a material suitable for use as said haptic portion to provide a second composite; and
   (d) machining said second composite to form said intraocular lens.

16. The method of claim 15 wherein said flexible element is selected from the group consisting of hydrated polyhydroxyethylacrylate, hydrated N-vinyl pyrrolidone, hydrated 3-hydroxypropyl methacrylate, hydrated methacrylic acid and hydrated acrylic acid.

17. The method of claim 15 wherein said flexible element is hydrated polyhydroxyethylacrylate.

18. The method of claim 15 further comprising the step of polymerizing about said first composite a polymerizable material, capable of forming said haptic portion, to form an outer layer about said first composite.

19. The method of claim 15 further comprising positioning said first composite in a mold, placing said polymerizable material in said mold about said composite, and polymerizing said polymerizable material.

20. The method of claim 15 wherein said surface is hydrolyzed by reaction with a strong acid or base.

* * * * *